(12) United States Patent
Hanauer et al.

(10) Patent No.: US 11,690,839 B2
(45) Date of Patent: Jul. 4, 2023

(54) TREATMENT OF IDIOPATHIC PULMONARY FIBROSIS

(71) Applicant: TAKEDA GMBH, Constance (DE)

(72) Inventors: Guido Hanauer, Constance (DE); Sham Nikam, Fujisawa (JP); Masatoshi Hazama, Fujisawa (JP)

(73) Assignee: TAKEDA GMBH, Constance (DE)

( * ) Notice: Subject to any disclaimer, the term of this patent is extended or adjusted under 35 U.S.C. 154(b) by 702 days.

(21) Appl. No.: 16/494,590

(22) PCT Filed: Mar. 14, 2018

(86) PCT No.: PCT/EP2018/056381
§ 371 (c)(1),
(2) Date: Sep. 16, 2019

(87) PCT Pub. No.: WO2018/167142
PCT Pub. Date: Sep. 20, 2018

(65) Prior Publication Data
US 2021/0113549 A1    Apr. 22, 2021

(30) Foreign Application Priority Data

Mar. 16, 2017   (EP) .................................. 17161340

(51) Int. Cl.
| | | |
|---|---|---|
| *A61K 31/473* | (2006.01) | |
| *A61P 11/00* | (2006.01) | |
| *A61K 9/20* | (2006.01) | |
| *A61K 9/48* | (2006.01) | |
| *A61K 31/192* | (2006.01) | |
| *A61K 31/4418* | (2006.01) | |
| *A61K 31/496* | (2006.01) | |
| *A61K 31/4985* | (2006.01) | |
| *A61K 31/506* | (2006.01) | |
| *A61K 31/517* | (2006.01) | |
| *A61K 31/519* | (2006.01) | |
| *A61K 31/53* | (2006.01) | |
| *A61K 39/395* | (2006.01) | |
| *A61K 45/06* | (2006.01) | |
| *A61K 39/00* | (2006.01) | |

(52) U.S. Cl.
CPC .......... *A61K 31/473* (2013.01); *A61K 9/2018* (2013.01); *A61K 9/2054* (2013.01); *A61K 9/2059* (2013.01); *A61K 9/2095* (2013.01); *A61K 9/4825* (2013.01); *A61K 9/4858* (2013.01); *A61K 9/4866* (2013.01); *A61K 31/192* (2013.01); *A61K 31/4418* (2013.01); *A61K 31/496* (2013.01); *A61K 31/4985* (2013.01); *A61K 31/506* (2013.01); *A61K 31/517* (2013.01); *A61K 31/519* (2013.01); *A61K 31/53* (2013.01); *A61K 39/3955* (2013.01); *A61K 45/06* (2013.01); *A61P 11/00* (2018.01); *A61K 2039/505* (2013.01)

(58) Field of Classification Search
None
See application file for complete search history.

(56) References Cited

U.S. PATENT DOCUMENTS

| | | | | |
|---|---|---|---|---|
| 8,324,391 B2 * | 12/2012 | Kautz | .................. | C07D 401/04 546/285 |
| 2014/0187555 A1 | 7/2014 | Leysen et al. | | |
| 2014/0213560 A1 | 7/2014 | Vakkalanka | | |

FOREIGN PATENT DOCUMENTS

| | | | | |
|---|---|---|---|---|
| WO | WO-2006065814 A1 * | 6/2006 | ............. | A61K 31/00 |
| WO | 2013021021 A1 | 2/2013 | | |
| WO | 2014115127 A1 | 7/2014 | | |

OTHER PUBLICATIONS

Taniguichi et al, European Journal Respiratory Journal , vol. 35, No. 4, pp. 821-829 (Year: 2010).*
Dunkem et al., Eur. J. Pharmacol., 2007, 572[1]:12-22.
Hatzelmann et al., Pulm. Pharmacol. Ther., 2010,23[4]:235-256.
Raghu et al., Am. J. Respir. Crit. Care Med., 1999, 159{4}:1061-1069.
Sabina et al., Multidiscip. Respir. Med., 2012, 7[1]:41.
PCT; App. No. PCT/EP2018/056381; International Search Report and Written Opinion dated May 4, 2018.

* cited by examiner

*Primary Examiner* — Zinna Northington Davis
(74) *Attorney, Agent, or Firm* — Barnes & Thornburg LLP; Ryan L. Marshall; William R. Boudreaux

(57) ABSTRACT

The present invention is directed to the treatment of idiopathic pulmonary fibrosis with (a) a phosphodiesterase 4 inhibitor or (b) a phosphodiesterase 4 inhibitor and a second active pharmaceutical ingredient.

11 Claims, 3 Drawing Sheets

Effect on Lung hydroxyproline content (Mean±SE, n=8-9, p-values by ANOVA test)

Effect on Body weight change

Inhibitory Effect of Compound A on TGF-β induced mRNA expression on pro-fibrotic markers in WI-38 human lung fibroblast cell line
(C: control; Mean±SD, n=4, #: $p<0.05$ vs forskolin/TGF-β group by William's test)

TREATMENT OF IDIOPATHIC PULMONARY FIBROSIS

CROSS REFERENCE TO RELATED APPLICATIONS

This application is a 371 national phase of PCT/EP2018/056381, filed Mar. 14, 2018. This application also claims priority under 35 U.S.C. § 119 to European Application No. 17161340.9, filed Mar. 16, 2017, the disclosures of which are incorporated, in their entirety, by this reference.

FIELD OF THE INVENTION

The present invention is directed to the treatment of idiopathic pulmonary fibrosis (IPF). More particularly, the present invention is directed to a) the use of a phosphodiesterase 4 inhibitor (sometimes abbreviated as PDE4 inhibitor in the present specification) or, b) the use of a phosphodiesterase 4 inhibitor in combination with a second active pharmaceutical ingredient for the treatment of idiopathic pulmonary fibrosis.

BACKGROUND OF THE INVENTION

IPF is known as a fatal disease by increasing the fibrosis in pulmonary alveolus interstitium and decreasing the respiratory function, due to continuous excessive extracellular matrix component induction derived from the dysfunction of alveolar epithelial cells. The prognosis from the primary diagnosis is quite bad. Survival rate for five years after the primary diagnosis is around 50%. Steroids and immunosuppressant agents are not effective for IPF. Currently, anti-fibrosis agents, such as pirfenidone, are used in the clinical practice, however, the efficacy is limited and adverse effects in digestive organs and photo toxicity are pointed out.

SUMMARY OF THE INVENTION

The present invention provides a pharmaceutical composition comprising a phosphodiesterase 4 (PDE4) inhibitor for use in the treatment of idiopathic pulmonary fibrosis.

The phosphodiesterase 4 inhibitor is selected from 5-((2R,4aR,10bR)-9-Ethoxy-2-hydroxy-8-methoxy-1,2,3,4,4a,10b-hexahydro-phenanthridin-6-yl)1-methyl-1H-pyridin-2-one (hereinafter referred to as "Compound A") and a pharmaceutically acceptable salt thereof.

DEFINITIONS

Figure 1A:
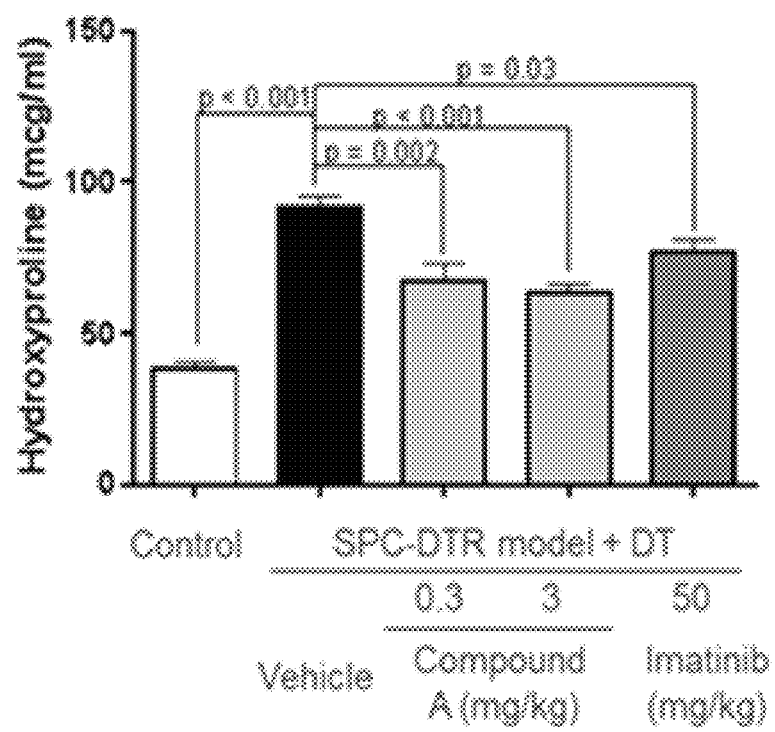
FIG. 1: Therapeutic effects of Compound A and Imatinib on lung fibrosis: Lung hydroxyproline content (FIG. 1A) and body weight changes (FIG. 1B) after treatment with Compound A or imatinib

In the present invention, the phrase "therapeutically effective amount" refers to the amount of active compound or pharmaceutical agent, or in the case of combination therapy, the combined amount of each compound or pharmaceutical agent, that elicits the biological or medicinal response that is being sought in a tissue, system, animal, individual, or human, by the researcher, veterinarian, medical doctor or other clinician.

As used herein, "mammal" refers to humans, mice, rats, rabbits, dogs, cats, bovines, horses, swine and monkeys, with preference given to humans.

As used herein, "pharmaceutically acceptable salt" refers to salts with bases and salts with acids.

Pharmaceutically acceptable salts which may be mentioned in connection with Compound A are the hydrochloride, fumarate, L-tartrate edisilate, esilate, hydrobromide and the tosylate salt of Compound A.

DETAILED DESCRIPTION OF THE INVENTION

The present invention provides a pharmaceutical composition comprising a phosphodiesterase 4 (PDE4) inhibitor for use in the treatment of idiopathic pulmonary fibrosis.

The phosphodiesterase 4 (PDE4) inhibitor used in the present invention is 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one or a pharmaceutically acceptable salt thereof.

The chemical name of 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one is for ease of reading at many occasions throughout this specification and the claims replaced by the expression "Compound A".

Compound A is disclosed in U.S. Pat. No. 8,324,391, which is hereby incorporated by reference in its entirety.

Pharmaceutically acceptable salts of Compound A are disclosed in U.S. Pat. No. 8,754,218, which is hereby incorporated by reference in its entirety, too. Examples of pharmaceutically acceptable salts of Compound A, which may be mentioned are the hydrochloride, the fumarate, the L-tartrate, the edisilate, the esilate, the hydrobromide and the tosylate salt of Compound A. Compound A is preferably used in its free form rather than in the form of a pharmaceutically acceptable salt thereof.

Compound A may be synthesized as disclosed in U.S. Pat. No. 8,324,391.

In several in vitro and in vivo (animal) experiments it has been found that Compound A shows a strong ameliorating effect on parameters relevant for treatment of idiopathic pulmonary fibrosis, such as lung hydroxyproline content.

It is believed that these effects observed in the animal experiments will translate in corresponding effects in the clinical setting in humans.

In a first aspect the invention relates to a pharmaceutical composition comprising a phosphodiesterase 4 (PDE4) inhibitor for use in the treatment of idiopathic pulmonary fibrosis, wherein the phosphodiesterase 4 (PDE4) inhibitor is selected from the group consisting of Compound A and a pharmaceutically acceptable salt thereof.

In a preferred embodiment of the first aspect of the invention, the phosphodiesterase 4 (PDE4) inhibitor is Compound A.

In a second aspect the invention relates to a pharmaceutical composition for use in the treatment of idiopathic pulmonary fibrosis, which comprises
(1) a phosphodiesterase 4 (PDE4) inhibitor in combination with
(2) a second active pharmaceutical ingredient,
wherein the phosphodiesterase 4 (PDE4) inhibitor is selected from the group consisting of compound A and a pharmaceutically acceptable salt thereof, and wherein the second active pharmaceutical ingredient (I) is selected from the group consisting of pirfenidone, nintedanib, tipelukast, vismodegib, riociguat, sildenafil, vardenafil, tadalafil, 2-(3-pentylphenyl)acetic acid (PBI-4050), 2-(3-(4-(1H-indazol-5-ylamino)quinazolin-2-yl)phenoxy)-N-propan-2-ylacetamide (KD-025), 2-((2-ethyl-6-(4-(2-(3-hydroxyazetidin-1-yl)-2-oxoethyl)piperazin-1-yl)-8-methylimidazo[1,2-a]pyridin-3-yl)(methylamino)-4-(4-fluorophenyl)thiazole-5-carbonitrile (GLPG-1690), CKD-942, SAR-156597 and a pharmaceutically acceptable salt thereof or (II) is selected from the group consisting of pamrevlumab, lebrikizumab, dectrekumab and BG-00011.

In a preferred embodiment of the second aspect of the invention, the phosphodiesterase 4 (PDE4) inhibitor is Compound A.

In a further preferred embodiment of the second aspect of the invention the second active pharmaceutical ingredient is pirfenidone.

In a further preferred embodiment of the second aspect of the invention the second active pharmaceutical ingredient is selected from the group consisting of nintedanib and a pharmaceutically acceptable salt of nintedanib, such as for example, the ethansulfonate (esilate) salt.

The present invention provides a pharmaceutical composition comprising Compound A or a pharmaceutically acceptable salt thereof (or Compound A or a pharmaceutically active pharmaceutical ingredient and a second active pharmaceutical ingredient) for use in the treatment of idiopathic pulmonary fibrosis. The pharmaceutical composition comprising Compound A or a pharmaceutically acceptable salt thereof (or Compound A or a pharmaceutically active pharmaceutical ingredient and a second active pharmaceutical ingredient) may be administered by a variety of administration routes. Administration can be, for example, oral, parenteral or transdermal. The preferred route of administration is oral.

The preferred dosage form for the therapy is the oral dosage form. Suitable oral dosage forms include tablets, capsules, powders, pills, solutions, suspensions, emulsions, pastes and granules. The most preferred oral dosage form is a tablet.

Dosage Information

Compound A or a pharmaceutically acceptable salt thereof may be administered once daily, twice daily three times a day or four times a day. Once daily administration is particularly preferred and may take place preferably in the morning or in the evening.

Compound A may be present in an oral dosage form intended for once daily administration in any amount from 0.1 mg to 2 mg, such as, but not limited to 0.1, 0.2, 0.25, 0.3, 0.4, 0.5, 0.6, 0.7, 0.75, 0.8, 0.9, 1.0, 1.25, 1.5, 1.75 or 2 mg.

If a twice or three times daily administration is intended instead of a once daily administration the above indicated amounts of Compound A can be divided by two, respectively three.

Corresponding amounts of a pharmaceutically acceptable salt of Compound A can easily be calculated by one of ordinary skill, depending on the choice of the respective salt.

In another preferred embodiment of the first aspect of the invention Compound A is administered at a daily dose of between 0.1 mg and 2 mg or the pharmaceutically acceptable salt of Compound A is administered at a daily dose corresponding to a Compound A daily dose of between 0.1 mg and 2 mg.

Pharmaceutical Formulations and Dosage Forms

When employed as pharmaceuticals, Compound A or a pharmaceutically acceptable salt thereof can be administered in the form of pharmaceutical composition. The pharmaceutical composition can be prepared in a manner well known in the pharmaceutical art and can be administered by a variety of routes. Administration can be pulmonary (e.g., by inhalation or insufflation of powders or aerosols, including by nebulizer, intratracheal, intranasal, epidermal and transdermal), oral or parenteral. Parenteral administration includes intravenous, subcutaneous, intraperitoneal or intramuscular injection, or infusion. Parenteral administration can be in the form of a single bolus dose or for example, can be by a continuous perfusion pump. Pharmaceutical composition and formulation for topical administration can include: transdermal patches; conventional pharmaceutical carriers; aqueous, powder or oily bases; thickeners; and/or the like which may be necessary or desirable.

This invention also includes pharmaceutical compositions which contain, as the active ingredient, one or more of the compounds of the invention in combination with one or more pharmaceutically acceptable carriers. Pharmaceutically acceptable carriers known in the art can be employed. In making the pharmaceutical composition of the invention, the active ingredients are typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the pharmaceutical composition can be in the form of tablets, pills, powders, lozenges, sachets, cachets, elixirs, suspensions, emulsions, solutions, syrups, aerosols (as a solid or in a liquid medium), soft and hard gelatin capsules, suppositories, sterile injectable solutions, and sterile packaged powders.

The pharmaceutical composition can be formulated in a unit dosage form, each dosage containing an amount of each active ingredient as described above. The term "unit dosage forms" refers to physically discrete units suitable as unitary dosages for human subjects and other mammals, each unit containing a predetermined quantity of active ingredient calculated to produce the desired therapeutic effect, in association with a suitable pharmaceutical excipient.

The compounds of the invention can be effective over a wide dosage range and are generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

| Pharmaceutical Preparation Example 1 (Production of capsule) | | |
|---|---|---|
| 1) | Compound A | 30 mg |
| 2) | Finely powdered cellulose | 10 mg |
| 3) | Lactose | 19 mg |
| 4) | Magnesium stearate | 1 mg |
| | Total | 60 mg |

1), 2), 3) and 4) are mixed, and packed into a gelatin capsule.

Pharmaceutical Preparation Example 2 (Production of tablets)

| | | |
|---|---|---|
| 1) | Compound A | 30 g |
| 2) | Lactose | 50 g |
| 3) | Corn starch | 15 g |
| 4) | Carboxymethylcellulose calcium | 44 g |
| 5) | Magnesium stearate | 1 g |
| | 1000 tablets, total | 140 g |

The total quantities of 1), 2) and 3) and 30 g of 4) are kneaded with water, the kneaded mixture is then subject to vacuum drying and granulation. To said granular powder is admixed 14 g of 4) and 1 g of 5) and the mixture subjected to tableting using a tableting machine. In this way, 1000 tablets containing 30 mg of compound of Compound A per tablet are obtained.

Pre-Clinical Studies

1) Comparison of Effects of PDE4 Inhibitor Compound A and Imatinib on Lung Fibrosis in IPF Mice Model (Therapeutic Treatment Regimen)

Experimental Protocol:

Animals: Transgenic mice expressing the diphtheria toxin receptor (DTR) under the control of the murine SPC promoter were generated on a C57BL/6 background (designated DTR+ mice) (Sisson et al, *Am J Respir Crit Care Med* 181:254-263, 2010). Control mice included littermates of SPC-DTR transgenic mice that were PCR-negative for the transgenic construct and C57BL/6 mice purchased from Jackson Laboratories (Bar Harbor, Me.). These control animals are designated DTR− and prior studies revealed that neither of these strains of mice develop significant fibrosis in response to diphtheria toxin (DT) administration.

Assessment of mouse genotypes: The presence of the DTR was detected using PCR for the SPC-DTR transgenic construct as previously described (Sisson et al, *Am J Respir Crit Care Med* 181:254-263, 2010).

Diphtheria Toxin Administration and Experimental Design: Six to ten week old mice were intraperitoneally injected with DT (Sigma Chemical, St. Louis, Mo.) once daily for 14 days at a dose of 12.5 µg/kg in 100 µL of PBS. Control groups received intraperitoneal PBS alone. Mice were weighed daily and on day 21 of the study protocol (7 days after the last dose of DT) blood and lungs were harvested 1 hour after the last drug administration. Lungs were sectioned and homogenized for hydroxyproline analysis.

Hydroxyproline assay: Hydroxyproline content of the lungs was measured as previously reported with modifications (Woessner et al. *Arch Biochem Biophys* 93:440-447, 1961).

DTR+ mice were administered daily doses of DT from day 1 through day 14. From day 11 through day 21, subsets of mice were treated with Compound A at doses of 0.3 mg/kg or 3.0 mg/kg (suspended in 0.5% methylcellulose and administered by oral gavage at a volume of 5 mL/kg) once daily, or imatinib at 50 mg/kg (10 mg/ml stock solution in PBS was administered by intraperitoneal injection at 5 mL/kg) once daily. Weight loss was tracked throughout the study, and the severity of lung fibrosis was assessed on day 21 by lung hydroxyproline concentration.

Figure 1B:
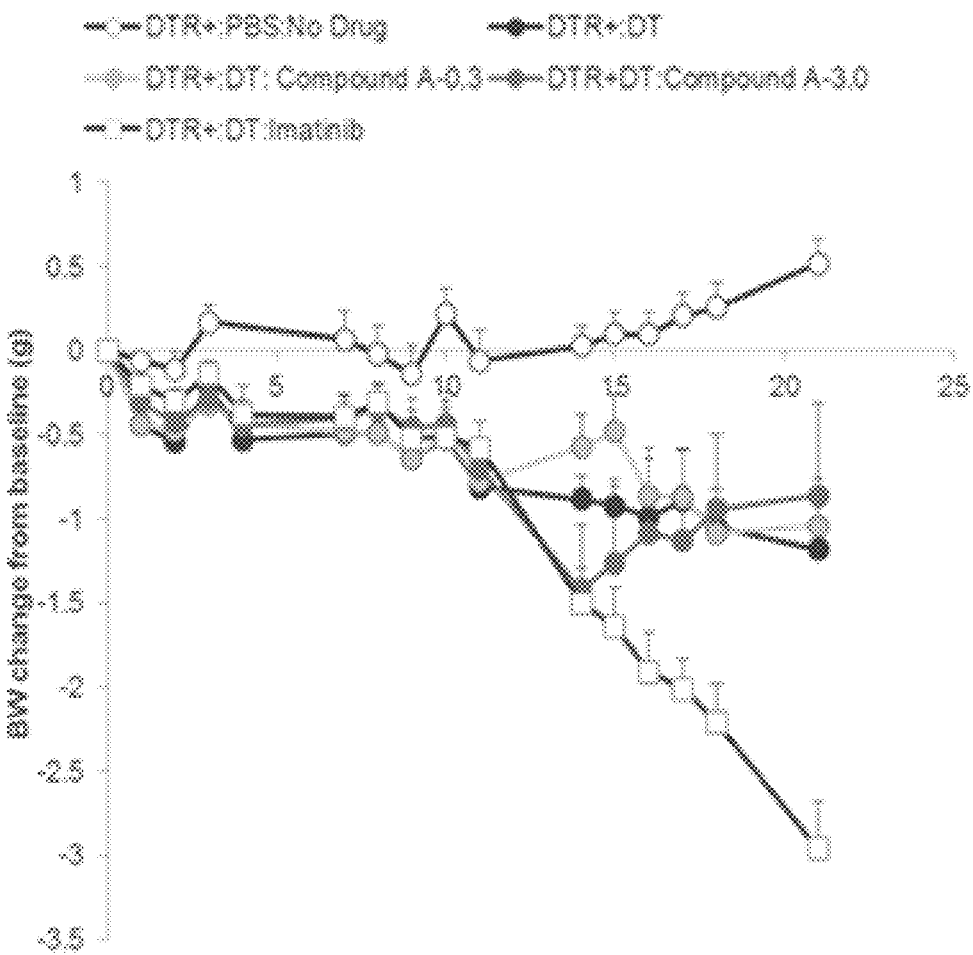

Results:

Effects of Compound A on lung fibrosis and body weight in the IPF model was examined in a therapeutic treatment regimen. The study results showed a robust and significant effect on suppression of hydroxyproline content already starting at the dose of 0.3 mg/kg of Compound A (FIG. 1A). In contrast thereto, Imatimib—although dosed at the 50 mg/kg—showed only a moderate efficacy. In addition, body weight reduction by induction of epithelial cell injury was not blunted by imatinib, while the blunting effect was shown for Compound A (FIG. 1B). These results suggest that Compound A may show clinical benefits in IPF patients.

2) In Vitro Effects of PDE4 Inhibitor Compound A in Human Lung Epithelial Cells

Experimental Protocol:

For gene expression assay, WI-38 human lung fibroblasts were suspended in Eagle's minimum essential medium (E-MEM, Invitrogen) containing 10% heat-inactivated fetal bovine serum (FBS) and seeded on 24 well plates as $0.5 \times 10^5$ cells/500 µL/well. Twenty-four hours after the seeding, medium was re-placed by E-MEM containing 0.5% FBS. Twenty-four hours after medium change, cells were treated with various concentration of Compound A. After 1 hour, cells were treated with TGF-β (3 ng/mL) and forskolin (1 µM). After the 24-hours incubation, total RNA was extracted from cell lysate using RNeasy 96 Kit (QIAGEN 74182). cDNA was amplified using High-Capacity cDNA Reverse Transcription Kit (ABI 4368813), and target gene mRNA was measured using TaqMan PCR with predesigned primers for type 1 collagen alpha 1 chain (Hs00164004_m1, Applied Biosystems), fibronectin (Hs00365052_m1, Applied Biosystems), connective tissue growth factor (Hs01026927_g1, Applied Biosystems), plasminogen activator inhibitor-1 (Hs00167155_m1, Applied Biosystems) and GAPDH (Hs02758991_g1, Applied Biosystems) as the endogenous reference. The target gene expression levels were normalized by mRNA expression of GAPDH and the data represent the relative mRNA levels to TGF-β/forskolin-treated group.

Figure 2:
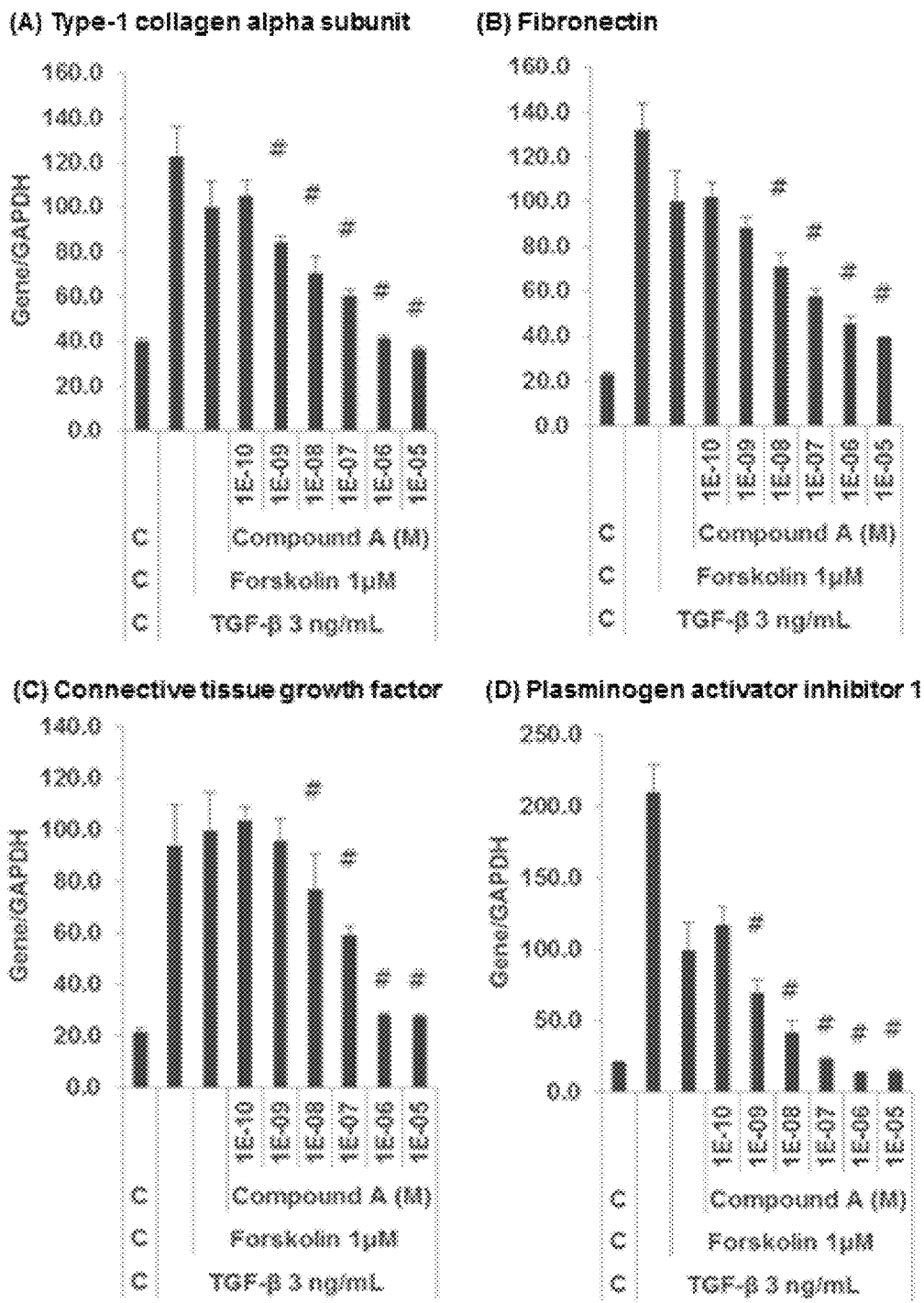
FIG. 2: Inhibitory effect of Compound A on TGF-β induced mRNA expression of pro-fibrotic markers in WI-38 human lung fibroblast cell line

Results:

The results are shown in FIG. 2. In WI-38 lung fibroblasts, mRNA expression of fibrotic markers including type 1 collagen alpha 1 subunit, fibronectin, connective tissue growth factor and plasminogen activator inhibitor-1 was increased by TGF-β treatment. Compound A significantly suppressed expression of fibrotic marker genes induced by TGF-β. These results indicate that Compound A has anti-fibrotic effects by inhibition of TGF-β-induced pro-fibrotic response in human lung cells.

Further aspects of the invention:

a) Method for the treatment of idiopathic pulmonary fibrosis comprising administering to a mammal (patient) in need thereof a therapeutically effective amount of a phosphodiesterase 4 (PDE4) inhibitor, wherein the phosphodiesterase 4 (PDE4) inhibitor is Compound A or a pharmaceutically acceptable salt thereof.

b) Method according to a), wherein the phosphodiesterase 4 (PDE4) inhibitor is Compound A.

c) Method for the treatment of idiopathic pulmonary fibrosis comprising administering to a mammal (patient) in need thereof a therapeutically effective amount of (1) a phosphodiesterase 4 (PDE4) inhibitor in combination with (2) a second active pharmaceutically ingredient wherein the phosphodiesterase 4 (PDE4) inhibitor is selected from the group consisting of compound A and a pharmaceutically acceptable salt thereof, and wherein the second active pharmaceutical ingredient (I) is selected from the group consisting of pirfenidone, nintedanib, tipelukast, vismodegib, riociguat, sildenafil, vardenafil, tadalafil, 2-(3-pentylphenyl)acetic acid (PBI-4050), 2-[3-[4-(1H-indazol-5-ylamino)

quinazolin-2-yl]phenoxy]-N-propan-2-ylacetamide (KD-025), 2-((2-ethyl-6-(4-(2-(3-hydroxyazetidin-1-yl)-2-oxoethyl)piperazin-1-yl)-8-methylimidazo[1,2-a]pyridin-3-yl)(methylamino)-4-(4-fluorophenyl)thiazole-5-carbonitrile (GLPG-1690), CKD-942, SAR-156597 and a pharmaceutically acceptable salt thereof or (II) is selected from the from the group consisting of pamrevlumab, lebrikizumab, dectrekumab and BG-00011.

d) Method according to c), wherein the phosphodiesterase 4 (PDE4) inhibitor is Compound A.

e) Method according to c) or d), wherein the second active pharmaceutical ingredient is pirfenidone.

f) Method according to c) or d), wherein the second active pharmaceutical ingredient is selected from the group consisting of nintedanib and a pharmaceutically acceptable salt thereof.

g) Method according to c) or d), wherein the second active pharmaceutical ingredient is nintedanib mesilate.

h) Use of a phosphodiesterase 4 (PDE4) inhibitor for the manufacture of a pharmaceutical composition for the treatment of idiopathic pulmonary fibrosis, wherein the phosphodiesterase 4 (PDE4) inhibitor is Compound A or a pharmaceutically acceptable salt thereof.

i) Use according to h) wherein the phosphodiesterase 4 (PDE4) inhibitor is Compound A.

j) Use of a phosphodiesterase 4 (PDE4) inhibitor in combination with a second active pharmaceutical ingredient for the manufacture of a pharmaceutical composition for the treatment of pulmonary idiopathic fibrosis,
wherein the phosphodiesterase 4 (PDE4) inhibitor is selected from the group consisting of compound A and a pharmaceutically acceptable salt thereof,
and wherein the second active pharmaceutical ingredient (I) is selected from the group consisting of pirfenidone, nintedanib, tipelukast, vismodegib, riociguat, sildenafil, vardenafil, tadalafil, 2-(3-pentylphenyl)acetic acid (PBI-4050), 2-[3-[4-(1H-indazol-5-ylamino)quinazolin-2-yl]phenoxy]-N-propan-2-ylacetamide (KD-025), 2-((2-ethyl-6-(4-(2-(3-hydroxyazetidin-1-yl)-2-oxoethyl)piperazin-1-yl)-8-methylimidazo[1,2-a]pyridin-3-yl)(methylamino)-4-(4-fluorophenyl)thiazole-5-carbonitrile (GLPG-1690), CKD-942, SAR-156597 and a pharmaceutically acceptable salt thereof or (II) is selected from the from the group consisting of pamrevlumab, lebrikizumab, dectrekumab and BG-00011.

k) Use according to j), wherein the phosphodiesterase 4 (PDE4) inhibitor is Compound A.

l) Use according to j) or k), wherein the second active pharmaceutical ingredient is pirfenidone.

m) Use according to j) or k), wherein the second active pharmaceutical ingredient is selected from the group consisting of nintedanib and a pharmaceutically acceptable salt thereof.

n) Use according to j) or k), wherein the second active pharmaceutical ingredient is nintedanib esilate.

The invention claimed is:

1. A method of treating idiopathic pulmonary fibrosis, comprising administering a pharmaceutical composition comprising 5-((2R,4aR,10bR)-9-ethoxy-2-hydroxy-8-methoxy-1,2,3,4,4a,10b-hexahydro-phenanthridin-6-yl)1-methyl-1H-pyridin-2-one (Compound A) or a pharmaceutically acceptable salt thereof to a patient in need thereof.

2. The method of claim 1, further comprising administering a second pharmaceutical ingredient selected from the group consisting of: pirfenidone, nintedanib, tipelukast, vismodegib, riociguat, sildenafil, vardenafil, tadalafil, 2-(3-pentylphenyl) acetic acid (PBI-4050), 2-[3-[4-(1H-indazol-5-ylamino)quinazolin-2-yl]phenoxy]-N-propan-2-ylacetamide (KD-025), 2-((2-ethyl-6-(4-(2-(3-hydroxyazetidin-1-yl)-2-oxoethyl)piperazin-1-yl)-8-methylimidazo[1,2-a]pyridin-3-yl)(methylamino)-4-(4-fluorophenyl)thiazole-5-carbonitrile (GLPG-1690), CKD-942, SAR-156597, and pharmaceutically acceptable salts thereof.

3. The method of claim 1, further comprising administering a second pharmaceutical ingredient which is pirfenidone.

4. The method of claim 1, further comprising administering a second active pharmaceutical ingredient which is nintedanib.

5. The method of claim 1, further comprising administering a second active pharmaceutical ingredient which is nintedanib esilate.

6. The method of claim 1, further comprising administering a second pharmaceutical ingredient selected from the group consisting of: riociguat, sildenafil, vardenafil, tadalafil, and pharmaceutically acceptable salts thereof.

7. The method of claim 1, further comprising administering a second pharmaceutical ingredient selected from the group consisting of: pamrevlumab, lebrikizumab, dectrekumab, BG-00011, and pharmaceutically acceptable salts thereof.

8. The method of claim 1, further comprising administering a second active pharmaceutical ingredient which is vismodegib.

9. The method of claim 1, further comprising the administering of Compound A as an aerosol.

10. The method of claim 1, further comprising the administering of Compound A once daily.

11. The method of claim 10, further comprising an oral dosage of Compound A from 0.1 mg to 2 mg per day.

* * * * *